(12) United States Patent
Welz-Biermann et al.

(10) Patent No.: US 7,709,656 B2
(45) Date of Patent: May 4, 2010

(54) IONIC LIQUIDS CONTAINING GUANIDINIUM CATIONS

(75) Inventors: Urs Welz-Biermann, Heppenheim (DE); Nikolai (Mykola) Ignatyev, Duisburg (DE); Helge Willner, Mühlheim/Ruhr (DE); German Bissky, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 529 days.

(21) Appl. No.: 10/559,183

(22) PCT Filed: Apr. 1, 2004

(86) PCT No.: PCT/EP2004/003459

§ 371 (c)(1), (2), (4) Date: Apr. 2, 2007

(87) PCT Pub. No.: WO2004/106288

PCT Pub. Date: Dec. 9, 2004

(65) Prior Publication Data

US 2007/0265453 A1    Nov. 15, 2007

(30) Foreign Application Priority Data

Jun. 2, 2003  (DE) .............................. 103 25 051

(51) Int. Cl.
    *C07D 233/44* (2006.01)
(52) U.S. Cl. ................................. 548/326.5
(58) Field of Classification Search ............... 548/326.5
    See application file for complete search history.

(56) References Cited

U.S. PATENT DOCUMENTS 5,827,602 A * 10/1998 Koch et al. .................. 429/328
2002/0015884 A1   2/2002 Schmidt et al.
2002/0022182 A1 * 2/2002 Heider et al. ................ 429/199
2003/0013021 A1   1/2003 Wariishi
2003/0080312 A1   5/2003 Carmichael et al.
2004/0144947 A1   7/2004 Garayt et al.

FOREIGN PATENT DOCUMENTS

EP    1 162 204 A   12/2001
WO    WO 98/50153 A   11/1998
WO    WO 02/092608 A   11/2002

OTHER PUBLICATIONS

Database Chemabs 'Online! Chemical Abstracts Service, Columbus, Ohio, US; Pentin, Yu.A. et al: "IR and Raman Spectral Data on the Structure of Metallic and Organic Salts of Cyanoform" XP002298932, found in STN Database accession No. 1979:5722 & Zhurnal Obshchei Khimii, 48(8), 1850-4, ISSN; 0044-460x.
Database Beilstein, Beilstein Institute for Organic Chemistry, Frankfurt-Main, Germany; XP002298933 & Haszeldine: J. Chem. Soc, 1958, pp. 1548-1551.
Database Beilstein, Beilstein Institute for Organic Chemistry, Frankfurt-Main, Germany; XP002298934, Database accession No. BRN 3833818 & Schaefer: Z. Anorg. Allg. Chem., 259, 1949, pp. 86-89.
MacFarlane, Douglas R. et al: "Low Viscosity Ionic Liquids Based on Organic Salts of the Dicyanamide Anion" Chemical Communications (Cambridge, United Kingdom), (16), 1430-1431 Coden: CHCOFS; ISSN: 1359-7345, 2001, XP002298931, the entire document.
Database Beilstein, Beilstein Institute for Organic Chemistry, Frankfurt-Main, Germany; XP002298935, Database Accession No. BRN 5206487, 5206487 & Schwoebel, et al.: Liebigs Ann. Chem., 5, 1984, pp. 900-903.
Database Beilstein, Beilstein Institute for Organic Chemistry, Frankfurt-Main, Germany; XP002298936, Database Accession No. BRN 5186648 & Kantlehner, W. et al.: Liebigs Ann. Chem., 1979, pp. 2096-2113.

* cited by examiner

*Primary Examiner*—Rei-tsang Shiao
(74) *Attorney, Agent, or Firm*—Millen, White, Zelano & Branigan, P.C.

(57) ABSTRACT

The present invention relates to salts having guanidinium cations, to processes for the preparation thereof, and to the use thereof as ionic liquids.

8 Claims, No Drawings

IONIC LIQUIDS CONTAINING GUANIDINIUM CATIONS

The present invention relates to salts containing guanidinium cations and various anions, to processes for the preparation of these salts, and to the use thereof as ionic liquids.

Ionic liquids or liquid salts are ionic species which consist of an organic cation and a generally inorganic anion. They do not contain neutral molecules and usually have melting points below 373 K. The prior art discloses a multiplicity of compounds which are used as ionic liquids. In particular, they are also the subject-matter of a series of patents and patent applications. Thus, solvent-free ionic liquids were disclosed for the first time by Hurley and Wier in a series of US patents (U.S. Pat. Nos. 2,446,331, 2,446,339 and 2,446,350). These "salts which are molten at room temperature" were based on $AlCl_3$ and a multiplicity of n-alkylpyridinium halides.

In recent years, some review articles on this topic have been published (R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionic liquids—novel solutions for transition-metal catalysis", *Angew. Chem.*, 112 (2000), 3926-3945; T. Welton "Room temperature ionic liquids. Solvents for synthesis and catalysis", *Chem. Rev.*, 92 (1999), 2071-2083; R. Hagiwara, Ya. Ito "Room temperature ionic liquids of alkylimidazolium cations and fluoroanions", *Journal of Fluorine Chem.*, 105 (2000), 221-227).

The properties of ionic liquids, for example melting point, thermal and electrochemical stability and viscosity, are greatly influenced by the nature of the anion. By contrast, the polarity and hydrophilicity or lipophilicity can be varied through a suitable choice of the cation/anion pair.

There is therefore a demand for novel ionic liquids having varied properties which facilitate additional possibilities regarding their use.

The object of the present invention is to provide novel stable salt-like compounds of low viscosity which can be used as ionic liquids, and a process for the preparation thereof.

This object is achieved by the provision of salts having guanidinium cations in which the positive charge is delocalised over a plurality of nitrogen atoms, in combination with selected anions in accordance with claim 1.

A publication by Peter J. Stang et al., J. Amer. Chem. Soc. 1981, 103 (16), 4837-4845, discloses the compound 1,3-dimethyl-2-diethylaminoimidazolidinium trifluoromethanesulfonate. Stang et al. synthesised a large number of dicationic ether salts of the formula $R^+$—O—$R^{+*}2CF_3SO_3^-$. These salts are described as thermally stable, but very hygroscopic. The reaction of bis-(1,3-dimethylimidazolinium-2-yl) ether ditriflate with diethylamine gave 1,3-dimethyl-2-diethylaminoimidazolidinium trifluoromethanesulfonate as illustrative secondary reaction of the dicationic ether salts.

W. Kantlehner et al., Liebigs Ann. Chem. 1984, 108-126, report on the difficulty of synthesising tetraalkylguanidinium salts, with the focus on the synthesis of tetraalkylguanidinium halides, which are highly hygroscopic. In order to characterise these halides, hexamethylguanidinium or hexaethylguanidinium chlorides, in particular, were converted into corresponding salts, in particular salts having the anions perchlorate, methylsulfate, hexa-fluorophosphate, tetrafluoroborate and nitrate.

EP 1 363 345 explicitly discloses the compound tetramethylguanidinium bis(trifluoromethanesulfonyl)imide and the use thereof as electrolyte. EP 1 363 345 was published after filing of the priority-establishing application DE 10325051.

Similar properties of this salt are assumed for compounds in which a proton or a plurality of protons of the guanidine unit are replaced by aliphatic substituents, such as ethyl, propyl, isopropyl, butyl, isobutyl, sec-butyl, tert-butyl or halogenated alkyl groups, such as partially or fully halogenated ethyl, propyl, isopropyl, butyl, isobutyl, sec-butyl or tert-butyl, where halogen is intended to be F, Cl, Br, I or At, but the asymmetry of the guanidinium cation is said to be retained. The asymmetry of the guanidinium cation is understood in the sense that all three nitrogen atoms may not be identically substituted. However, alicyclic and aromatic groups may also be substituents of a proton or some protons of the guanidinium, in particular which form a mono-, bi- or tricyclic ring. An example thereof that is mentioned is 1-methyl-7-n-propyl-1,5,7-triazabicyclo[4.4.0]dec-5-enium. Suitable anions, besides bis(trifluoromethanesulfonyl)imide, are also claimed to be hexafluorophosphate, tetrafluoroborate and trifluoromethanesulfonate (triflate) or trifluoromethanesulfonyltrifluoroacetylimide, trifluoromethanesulfonylpentafluoroethanesulfonylimide or closocarborates, such as $B_9H_9CH^-$, $B_{11}H_{22}CH^-$, closoborates, such as $B_{10}H_{10}^{2-}$ and $B_{12}H_{12}^{2-}$, and halogenated derivatives thereof, $AsF_6^-$, $SbF_6^-$, $ClO_4^-$, $O_2^-$, $AlCl_4^-$, $GaCl_4^-$, $C(SO_2CF_3)_3^-$, $SCN^-$, $C_6F_5SO_3^-$, $O_2CCF_3^-$, $SO_6F^-$ and $B(C_6H_5)_4^-$.

N. M. M. Mateus et al., Green Chem. 2003, 5, 347-352, disclose N,N-dimethyltetraalkylguanidinium salts and the preparation thereof, as revealed by the following reaction scheme:

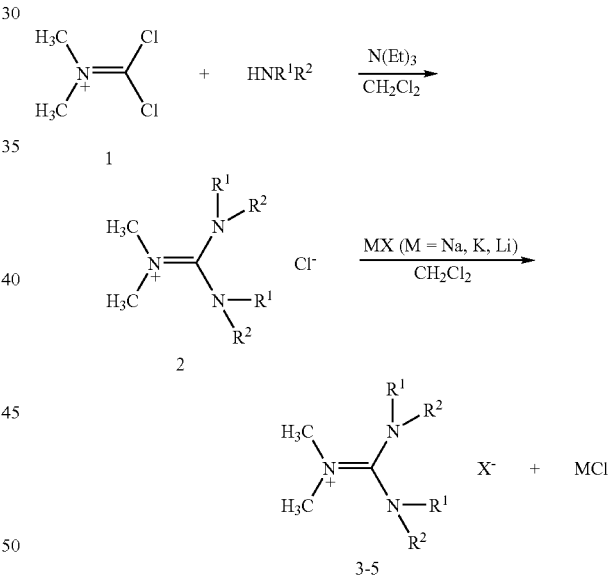

Compounds 3: $X^-=PF_6^-$, compounds 4: $X^-=BF_4^-$,
compounds 5: $X^-=[(CF_3SO_3)_2N]^-$,
a: $R^1=R^2=$n-butyl,
b: $R^1=$methyl, $R^2=$n-butyl,
c: $R^1=$ethyl, $R^2=$n-butyl,
d: $R^1=R^2=$n-hexyl,
e: $R^1=R^2=$n-octyl.

These N,N-dimethylguanidinium salts are furthermore described as a new generation of ionic liquids. A viscosity is only quoted for compound 5d, but is very high at 346 cP at 25° C.

The object of providing stable salt-like compounds of low viscosity which can be used as ionic liquids is achieved in accordance with the invention by salts having guanidinium cations in which the positive charge is delocalised over a plurality of nitrogen atoms, in accordance with the general formula (1)

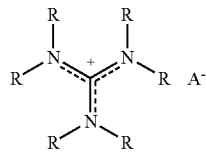

The groups R here have the meaning of
H
straight-chain or branched alkyl having 1-20 C atoms, or in the case of $A^- = [(C_2F_5)_3PF_3]^-$ straight-chain or branched alkyl having 2-20 C atoms or
saturated, partially or fully unsaturated cycloalkyl having 3-7 C atoms, which may be substituted by alkyl groups having 1-6 C atoms, in particular phenyl,
where the R are in each case identical or different,
where up to four R may be connected to one another in pairs by a single or double bond,
where one or more R may be partially or fully substituted by halogens, in particular —F and/or —Cl, or partially by —CN or —NO$_2$,
and where one or two non-adjacent carbon atoms of the R may be replaced by atoms and/or atom groups selected from the group —O—, —C(O)—, —C(O)O—, —S—, —S(O)—, —SO$_2$—, —SO$_2$O—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N—, where R'=unfluorinated, partially or perfluorinated $C_1$- to $C_6$-alkyl, $C_3$- to $C_7$-cycloalkyl, unsubstituted or substituted phenyl or an unsubstituted or substituted heterocycle,
and $A^-$ is selected from the group consisting of:
[(FSO$_2$)$_2$N]$^-$, [R$^F$CF$_2$SO$_3$]$^-$, [(R$^{F'}$SO$_2$)$_2$N]$^-$, [(R$^{F'}$SO$_2$)$_3$C]$^-$, [(FSO$_2$)$_3$C]$^-$, [R$^F$CF$_2$C(O)O]$^-$, [P(C$_n$F$_{2n+1-m}$H$_m$)$_y$F$_{6-y}$]$^-$, [P(C$_6$F$_5$)$_y$F$_{6-y}$]$^-$, [R$^F$$_2$P(O)O]$^-$, [R$^F$P(O)O$_2$]$^{2-}$, [BF$_z$R$^F$$_{4-z}$]$^-$, [BF$_z$(CN)$_{4-z}$]$^-$, [N(CF$_3$)$_2$]$^-$, [N(CN)$_2$]$^-$, [C(CN)$_3$]$^-$ or

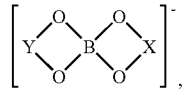

where
R$^F$=perfluorinated and straight-chain or branched alkyl having 1-20 C atoms, preferably having 1-12 C atoms,
perfluorinated and straight-chain or branched alkenyl having 2-20 C atoms and one or more double bonds,
perfluorinated and straight-chain or branched alkynyl having 2-20 C atoms and one or more triple bonds,
perfluorinated and saturated, partially or fully unsaturated cycloalkyl having 3-7 C atoms, in particular phenyl, which may be substituted by perfluoroalkyl groups,
where a plurality of R$^F$ may in each case be identical or different,
where the R$^F$ may be connected to one another in pairs by a single or double bond,
and where one or two non-adjacent carbon atoms of the R$^F$ which are not in the α-position to the heteroatom may be replaced by atoms and/or atom groups selected from the group —O—, —SO$_2$— and —NR'— or by the end group —SO$_2$X', where R'=unfluorinated, partially or perfluorinated $C_1$- to $C_6$-alkyl, $C_3$- to $C_7$-cycloalkyl, unsubstituted or substituted phenyl, including —C$_6$F$_5$, or an unsubstituted or substituted heterocycle, and X'=F, Cl or Br, and R$^{F'}$=perfluorinated and straight-chain or branched alkyl having 2-20 C atoms,
perfluorinated and straight-chain or branched alkenyl having 2-20 C atoms and one or more double bonds,
perfluorinated and straight-chain or branched alkynyl having 2-20 C atoms and one or more triple bonds,
perfluorinated and saturated, partially or fully unsaturated cycloalkyl having 3-7 C atoms, in particular phenyl, which may be substituted by perfluoroalkyl groups,
where a plurality of R$^{F'}$ may in each case be identical or different,
where the R$^{F'}$ may be connected to one another in pairs by a single or double bond,
and where one or two non-adjacent carbon atoms of the R$^{F'}$ which are not in the α-position to the heteroatom may be replaced by atoms and/or atom groups selected from the group —O—, —SO$_2$— and —NR'— or by the end group —SO$_2$X', where R'=unfluorinated, partially or perfluorinated $C_1$- to $C_6$-alkyl, $C_3$- to $C_7$-cycloalkyl, unsubstituted or substituted phenyl, including —C$_6$F$_5$, or an unsubstituted or substituted heterocycle, and X'=F, Cl or Br,
n=1 to 20, preferably 1 to 12, and
m=0, 1, 2 or 3 and
y=1, 2, 3 or 4 and
z=0, 1, 2 or 3 and
—X— and —Y— are in each case identical or different and denote —C(O)—C(O)—, —C(O)—(CH$_2$)$_q$—C(O)—, where q=1, 2 or 3, —C(O)—(CF$_2$)$_q$—C(O)—, where q=1, 2 or 3, —C(CF$_3$)$_2$—C(CF$_3$)$_2$—,

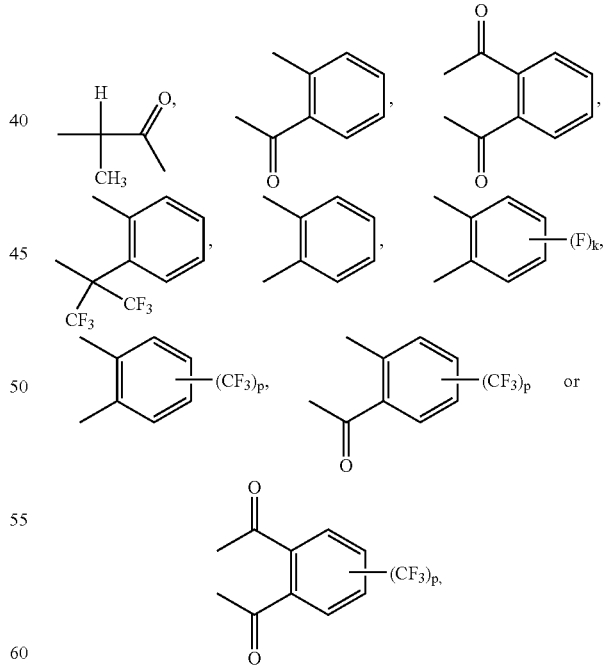

where k=1, 2, 3 or 4 and p=1 or 2.
For the purposes of the present invention, fully unsaturated substituents are also taken to mean aromatic substituents.
The compounds according to the invention are distinguished, in particular, by very stable cations.

The compounds according to the invention are accordingly salts which have an optionally substituted guanidinium cation.

Besides hydrogen, suitable substituents R of the guanidinium cation are, in accordance with the invention: $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl. The six substituents R of the guanidinium cation according to the invention may be identical or different here.

The $C_1$-$C_6$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl or hexyl, if desired difluoromethyl, trifluoromethyl, pentafluoroethyl, heptafluoropropyl or nonafluorobutyl.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, CN or $NO_2$.

The substituents R may be partially or fully substituted by halogen atoms, in particular by F and/or Cl, or partially by CN or $NO_2$. Furthermore, the substituents R may contain one or two mutually adjacent heteroatoms or atom groups selected from the group —O—, —C(O)—, —C(O)O—, —S—, —S(O)—, —$SO_2$—, —$SO_2$O—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N—, where R' can be an unfluorinated, partially or perfluorinated $C_1$- to $C_6$-alkyl, $C_3$- to $C_7$-cycloalkyl, unsubstituted or substituted phenyl or an unsubstituted or substituted heterocycle which are not in the α-position to a nitrogen atom of the guanidinium.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR"$_2$, $SO_2$OR", $SO_2$X', $SO_2$NR"$_2$, $SO_3$H or NHC(O)R", where X' denotes F, Cl or Br, and R" denotes an unfluorinated, partially or perfluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-aminophenyl, o-, m- or p-(N,N-dimethylamino)phenyl, o-, m- or p-nitrophenyl, o-, m- or p-hydroxyphenyl, o-, m- or p-methoxyphenyl, o-, m- or p-ethoxyphenyl, o-, m- or p-(trifluoromethyl)phenyl, o-, m- or p-(trifluoromethoxy)phenyl, o-, m- or p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethoxyphenyl.

In R', heterocycle is taken to mean a saturated or unsaturated mono- or bi-cyclic heterocyclic radical having 5 to 13 ring members, where 1, 2 or 3 N and/or 1 or 2 S or O atoms may be present, and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR"$_2$, $SO_2$OR", $SO_2$X', $SO_2$NR"$_2$, $SO_3$H or NHC(O)R", where X' and R" have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, 4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1 H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4-, or 9-carbazolyl, 1-, 2-, 3-, 4-, 5-, 6-, 7-, 8- or 9-acridinyl, 3-, 4-, 5-, 6-, 7-, or 8-cinnolinyl, 2-, 4-, 5-, 6-, 7- or 8-quinazolinyl or 1-, 2- or 3-pyrrolidinyl.

Without restricting generality, examples of substituents R of the guanidinium cation are:

—$CH_3$, —$C_2H_5$, —$C_3H_7$, —$CH(CH_3)_2$, —$C_4H_9$, —$C(CH_3)_3$, —$C_5H_{11}$, —$C_6H_{13}$, —$C_7H_{15}$, —$C_8H_{17}$, —$C_9H_{19}$, —$C_{10}H_{21}$, —$C_{12}H_{25}$, —$C_{20}H_{41}$, —$OCH_3$, —OCH$(CH_3)_2$, —$CH_2OCH_3$, —$C_2H_4OCH(CH_3)_2$, —$C_2H_4SC_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —$CH_2N(H)C_2H_5$, —$C_2H_4N(H)C_2H_5$, —$CH_2N(CH_3)CH_3$, —CN, —$C_2H_4N(CH_3)CH_3$, —$NH_2$, —$NHC_2H_5$, —$N(CH_3)_2$, —$N(CH_3)C_2H_5$, —$N(CH_3)CF_3$, —O—$C_4H_8$—O—$C_4H_9$, —$CF_3$, —$C_2F_5$, —$C_3F_7$, —$C_4F_9$, —$C(CF_3)_3$, —$CF_2SO_2CF_3$, —$C_2F_4N(C_2F_5)C_2F_5$, —$CHF_2$, —$CH_2CF_3$, —$C_2F_2H_3$, —$C_3FH_6$, —$CH_2C_3F_7$, —$C(CFH_2)_3$, —$CH_2C(O)OH$, —$CH_2C_6H_5$, —$CH_2C(O)CH_3$, —$CH_2C(O)C_2H_5$, —$CH_2C(O)OCH_3$, $CH_2C(O)OC_2H_5$, —$C(O)CH_3$, —$C(O)C_6H_5$, —$C(O)OCH_3$, —$C(O)OC_2H_5$, $P(O)(C_2H_5)_2$, $P(O)[N(C_2H_5)_2]_2$,

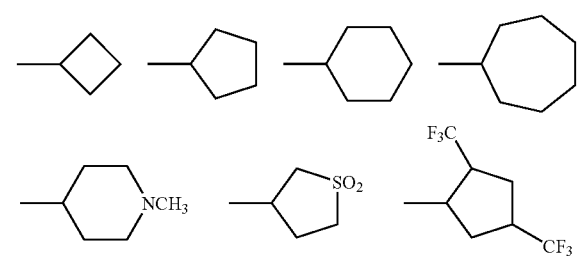

-continued

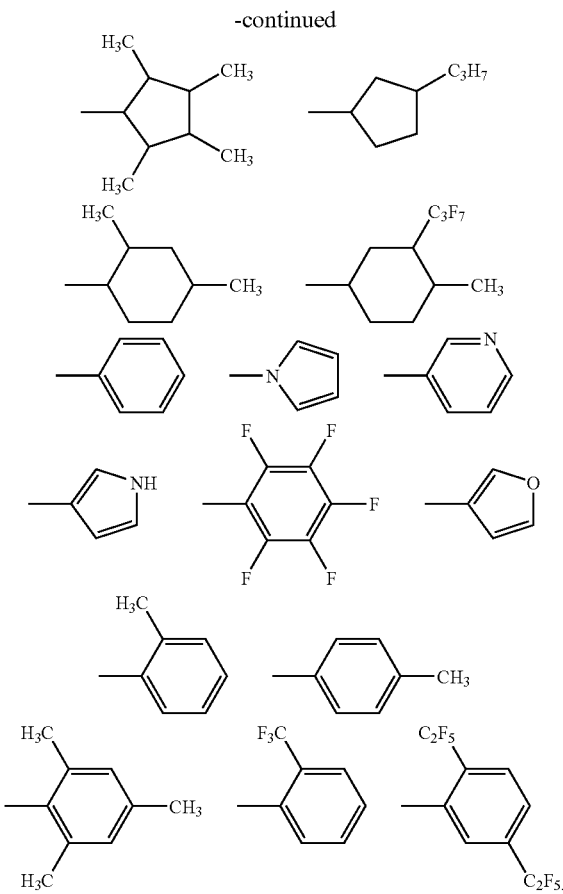

Up to four substituents R may also be connected in pairs in such a way that mono-, bi- or polycyclic cations are formed.

Without restricting generality, examples of such guanidinium cations are:

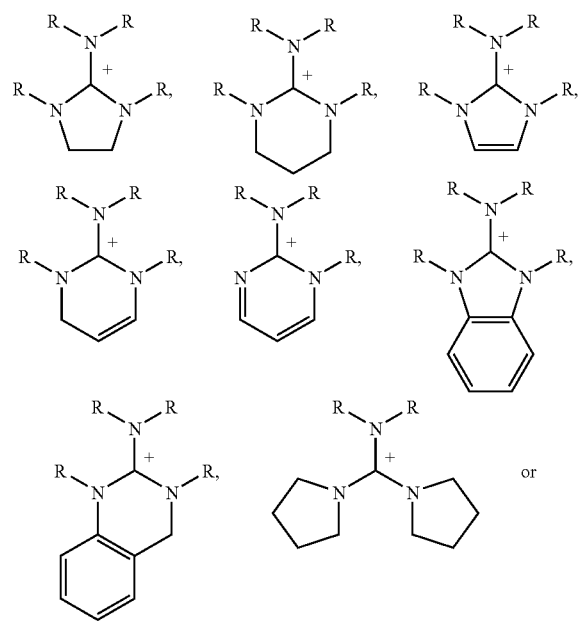

-continued

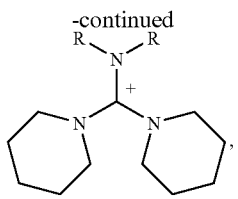

where the substituents R can have an above-mentioned or particularly preferred meaning.

If desired, the carbocyclic or heterocyclic rings of the above-mentioned guanidinium cations may also be substituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR''$_2$, $SO_2$OR'', $SO_2$NR''$_2$, $SO_2$X', $SO_3$H or NHC(O)R'', where X' and R'' have a meaning indicated above, substituted or unsubstituted phenyl or an unsubstituted or substituted heterocycle.

The anion $A^-$ of the salts according to the invention is selected from $[(FSO_2)_2N]^-$, $[R^FCF_2SO_3]^-$, $[(R^{F'}SO_2)_2N]^-$, $[(R^{F'}SO_2)_3C]^-$, $[(FSO_2)_3C]^-$, $[R^FCF_2C(O)O]^-$, $[P(C_nF_{2n+1-m}H_m)_yF_{6-y}]^-$, $[P(C_6F_5)_yF_{6-y}]^-$, $[R^F_2P(O)O]^-$, $[R^FP(O)O_2]^{2-}$, $[BF_zR^F_{4-z}]^-$, $[BF_z(CN)_{4-z}]^-$, $[N(CF_3)_2]^-$, $[N(CN)_2]^-$, $[C(CN)_3]^-$ or

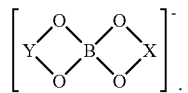

In accordance with the invention, suitable organic groups $R^F$ or $R^{F'}$ of the anion are: $C_1$- or $C_2$- to $C_{20}$-, in particular $C_1$- or $C_2$- to $C_{12}$-alkyl groups respectively, $C_2$- to $C_{20}$-, in particular $C_2$- to $C_{12}$-alkenyl- or -alkynyl groups and saturated or unsaturated, i.e. also aromatic, $C_3$- to $C_7$-cycloalkyl groups, which may be substituted by $C_1$- to $C_6$-alkyl groups, in particular phenyl, where all the groups listed are in perfluorinated form.

A straight-chain or branched alkenyl having 2 to 20 C atoms, where a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

In the case where a plurality of $R^F$ or $R^{F'}$ are present in one anion, these may also be connected in pairs by single or double bonds in such a way that bi- or polycyclic anions are formed.

Furthermore, the substituents $R^F$ or $R^{F'}$ may contain one or two atoms or atom groups which are not adjacent to one another and are not in the α-position to the heteroatom, selected from the group —O—, —$SO_2$— and —NR'—, or the end group —$SO_2$X', where R' can be unfluorinated, partially or perfluorinated $C_1$- to $C_6$-alkyl, $C_3$- to $C_7$-cycloalkyl, unsubstituted or substituted phenyl, including —$C_6F_5$, or an unsubstituted or substituted heterocycle, and X'=F, Cl or Br.

Without restricting generality, examples of substituents $R^F$ and $R^{F'}$ of the anion are:

—$CF_3$, —$C_2F_5$, —$C_3F_7$, —$C_4F_9$, —$C(CF_3)_3$, —$CF_2N(CF_3)CF_3$, —$CF_2OCF_3$, —$CF_2S(O)CF_3$, —$CF_2SO_2CF_3$, —$C_2F_4N(C_2F_5)C_2F_5$, CF=$CF_2$, —$C(CF_3)$=$CFCF_3$, —$CF_2CF$=$CFCF_3$, —$CF$=$CFN(CF_3)CF_3$ or —$CF_2SO_2F$, —$C(CF_3)$=$CFCF_3$, —$CF_2CF$=$CFCF_3$ or —$CF$=$CFN(CF_3)CF_3$.

$R^F$ is preferably pentafluoroethyl, heptafluoropropyl or nonafluorobutyl. $R^{F'}$ is preferably trifluoromethyl, pentafluoroethyl, heptafluoropropyl or nonafluorobutyl.

Without restricting generality, some examples of anions according to the invention are shown below: $[(FSO_2)_2N]^-$, $[CF_3CF_2SO_3]^-$, $[(C_2F_5SO_2)_2N]^-$, $[(C_2F_5SO_2)_3C]^-$, $[(FSO_2)_3C]^-$, $[CF_3CF_2C(O)O]^-$, $[P(C_2F_5)_3F_3]^-$, $[P(CF_3)_3F_3]^-$, $[P(C_2F_4H)(CF_3)_2F_3]^-$, $[P(C_2F_3H_2)_3F_3]^-$, $[P(C_2F_5)(CF_3)_2F_3]^-$, $[P(C_6F_5)_3F_3]^-$, $[P(C_3F_7)_3F_3]^-$, $[P(C_4F_9)_3F_3]^-$, $[P(C_2F_5)_2F_4]^-$, $[(C_2F_5)_2P(O)O]^-$, $[(C_2F_5)P(O)O_2]^{2-}$, $[P(C_6F_5)_2F_4]^-$, $[(CF_3)_2P(O)O]^-$, $[(C_4F_9)_2P(O)O]^-$, $[CF_3P(O)O_2]^{2-}$, $[BF_3(CF_3)]^-$, $[BF_2(C_2F_5)_2]^-$, $[BF_3(C_2F_5)]^-$, $[BF_2(CF_3)_2]^-$, $[B(C_2F_5)_4]^-$, $[BF_3(CN)]^-$, $[BF_2(CN)_2]^-$, $[B(CN)_4]^-$, $[B(CF_3)_4]^-$, $[N(CF_3)_2]^-$, $[N(CN_2)_2]^-$, $[C(CN)_3]^-$,

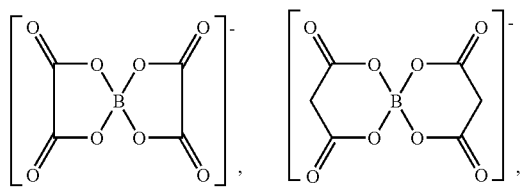,

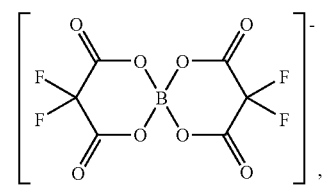,

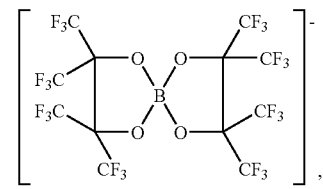,

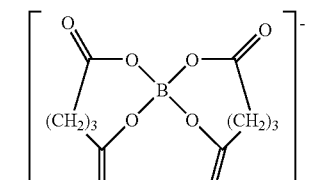,

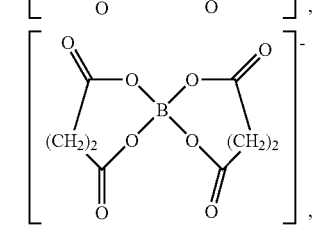,

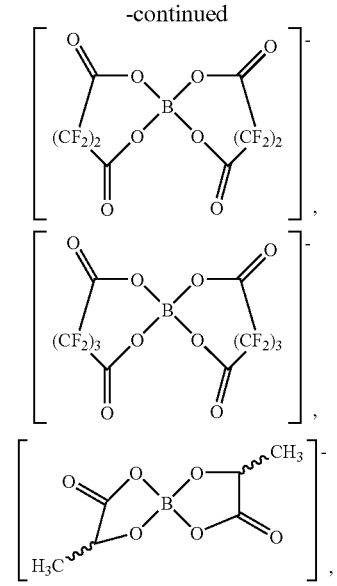,

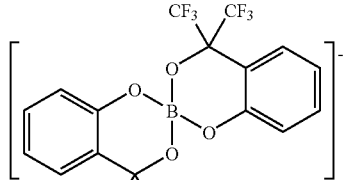 or

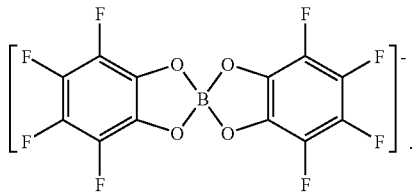.

Very preferred anions of this group are $[P(C_nF_{2n+1-m}H_m)_yF_{6-y}]^-$, $[BF_zR^F_{4-z}]^-$ and $[BF_z(CN)_{4-z}]^-$, where n, m, y and z have one of the above-mentioned meanings, for example $[B(CN)_4]^-$, $[(C_2F_5)_3PF_3]^-$, $[(C_2F_5)_2PF_4]^-$, $[(C_4F_9)_3PF_3]^-$, $[(C_3F_7)_3PF_3]^-$, $[B(C_2F_5)F_3]^-$ or $[B(CF_3)_4]^-$. Very particularly preferred anions of this group are $[B(CN)_4]^-$, $[(C_2F_5)_3PF_3]^-$ or $[B(C_2F_5)F_3]^-$.

In accordance with the invention, preference is given to a group of salts of the formula (1) in which the substituents R of the guanidinium cation denote hydrogen or a straight-chain or branched alkyl group having 1-12 C atoms, in particular having 1-4 C atoms, and $A^-$ has a meaning indicated for the formula (1) or a preferred or particularly preferred meaning.

In accordance with the invention, preference is given to a group of salts of the formula (1) in which the substituents R of the guanidinium cation are selected from the group methyl, ethyl, n-propyl, isopropyl, n-butyl, tert-butyl, sec-butyl, phenyl and cyclohexyl, and $A^-$ has a meaning indicated for the formula (1) or a preferred or particularly preferred meaning.

In accordance with the invention, preference is given to a group of salts of the formula (1) in which at least two substituents R are connected to one another by single or double bonds in such a way that a monocyclic cation is formed, and $A^-$ has a meaning indicated for the formula (1) or a preferred or particularly preferred meaning.

In accordance with the invention, particular preference is given to a group of salts in which the substituents R each, independently of one another, denote hydrogen, methyl, ethyl, n-propyl, isopropyl, n-butyl or i-butyl or two substituents R are connected to one another in such a way that an imidazolidinium cation is formed, and $A^-$ has a meaning indicated for the formula (1) or a preferred or particularly preferred meaning.

The present invention secondly relates to a process for the preparation of the salts having guanidinium cations of the general formula (1) according to the invention. To this end, a guanidine $(NR_2)_2C=(NR)$ or a guanidinium salt $C(NR_2)_3^+ X^-$ is reacted with an acid AH, a salt $Kt^+ A^-$ or an ester AR.

The anion $X^-$ of the reacting guanidinium salt is selected here from the group $F^-$, $Cl^-$, $Br^-$, $I^-$, $[HF_2]^-$, $[CN]^-$, $[SCN]^-$, $[CH_3COO]^-$, $[CF_3COO]^-$, $[CF_3SO_3]^-$, $[CH_3OSO_3]^-$, $[SiF_6]^{2-}$, $[BF_4]^-$, $[SO_4]^{2-}$, $[NO_3]^-$, $[C_2H_5OSO_3]^-$, tosylates, malonates, substituted malonates and $[CO_3]^-$. $X^-$ is preferably $F^-$, $Cl^-$, $Br^-$, $I^-$, $[HF_2]^-$, $[CH_3OSO_3]^-$, $[CF_3COO]^-$, $[CF_3SO_3]^-$ or $[CO_3]^-$, particularly preferably $Cl^-$, $Br^-$, $[CH_3OSO_3]^-$ or $[CF_3SO_3]^-$.

The groups and substituents A and R here are defined like those of the general formula (1), and Kt is an alkali or alkaline earth metal, where, for the ester AR, perhalogenated alkyl groups having 1-20 C atoms, cycloalkyl groups having 3-7 C atoms, alkenyl groups having 2-20 C atoms and alkynyl groups having 2-20 C atoms are excluded for the meaning of the substituents R.

The reaction is preferably carried out at a temperature at which at least one of the components is liquid. The reaction is particularly preferably carried out in a temperature range in which the reaction mixture is liquid.

The reaction of the guanidine or guanidinium salt with an acid AH or a salt $Kt^+ A^-$ can be carried out in polar inorganic or organic solvents, for example water, acetonitrile, dimethoxyethane, methanol, dimethylformamide, propionitrile or dichloromethane. The reaction with an ester, an acid or a salt can be carried out in nonpolar organic solvents as diluent, for example hexane or pentane, or without solvents, for example in the salt melt. The alkylation of the guanidine using an ester can be carried out in a non-basic solvent, preferably hexane, pentane or dichloromethane. In accordance with the invention, solvent mixtures can also be used instead of pure solvents.

In accordance with the invention, the reagents in the alkylation can be reacted with an up to five-fold excess of one of the reactants, in particular of the alkylating agent. However, the reactants are preferably employed in equimolar amount.

The salts according to the invention can be isolated with very good yields, generally greater than 80%, preferably greater than 90%.

The present invention furthermore relates to a process for the preparation of a salt having a guanidinium cation of the general formula (1) and a $[BF_4]^-$ anion, where R has a meaning indicated for the formula (1) or a preferred meaning, which process can furthermore be used for the preparation of the guanidinium salts according to the invention. In this process, firstly a guanidinium chloride $C(NR_2)_3^+ Cl^-$ or a guanidinium bromide $C(NR_2)_3^+ Br^-$, where the radicals R are defined in accordance with the general formula (1), is reacted with anhydrous HF, and the guanidinium fluoride formed in situ is subsequently reacted with boron trifluoride etherate $BF_3 \cdot Et_2O$.

Guanidinium tetrafluoroborates are advantageously formed in this process according to the invention with a reduced amount of chloride ions, i.e. the proportion of chloride ions is <100 ppm, preferably <50 ppm.

The anhydrous hydrofluoric acid functions both as solvent and also as reagent in this reaction.

The reaction is preferably carried out at a temperature at which at least one of the components is liquid. The reaction is particularly preferably carried out in a temperature range in which the reaction mixture is liquid.

In accordance with the invention, the boron trifluoride etherate can be employed in an excess of up to 10% in relation to the guanidinium salt. However, the reactants are preferably employed in equimolar amount.

All compounds according to the invention have a salt-like character, relatively low melting points (usually below 100° C.) and can be used as ionic liquids. In particular, they have, as described above, particularly low viscosities.

The salts according to the invention can be employed as solvents for many synthetic or catalytic reactions, for example Friedel-Crafts acylation and alkylation, Diels-Alder cycloadditions, hydrogenation and oxidation reactions or Heck reactions.

The use of the compounds according to the invention as non-aqueous electrolyte, optionally in combination with other electrolytes known to the person skilled in the art, is also possible.

In addition, the salts according to the invention can be used as non-aqueous polar substances in suitable reactions as phase-transfer catalyst, as surfactant (surface-active agent) or as medium for the heterogenisation of homogeneous catalysts.

They are furthermore suitable as desiccants and as separating agents for gases. This use is particularly preferred for the triflates according to the invention.

The complete disclosure content of all applications, patents and publications mentioned above and below is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. in a Bruker Avance 300 spectrometer with a 5 mm $^1$H/BB broad-band head with deuterium lock, unless indicated otherwise in the examples. Measurement frequencies of the various nuclei are: $^1$H: 300.13 MHz, $^{11}$B: 96.92 MHz, $^{19}$F: 282.41 MHz and $^{31}$P: 121.49 MHz. The referencing method is indicated separately for each spectrum or for each data set.

EXAMPLE 1

Hexamethylguanidinium triflate

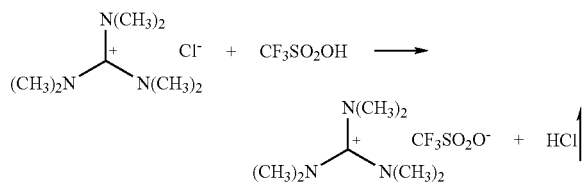

9.50 g (52.9 mmol) of hexamethylguanidinium chloride are dissolved in 100 cm³ of water. 8.03 g (53.5 mmol) of trifluoromethanesulfonic acid are added at room temperature while the reaction mixture is stirred using a magnetic stirrer.

The water is removed in a rotary evaporator together with volatile by-products. The residue is washed twice with 50 cm³ of diethyl ether and dried at 50-60° C. under a vacuum of 7.0 Pa, giving 14.8 g of a solid material (m.p.=174-176° C.). The yield of hexamethylguanidinium triflate is 95.4%, based on hexamethylguanidinium chloride.

$^{19}$F NMR (reference: CCl$_3$F—internal standard; solvent: CD$_3$CN): −77.89 s (CF$_3$).

$^1$H NMR (reference: TMS; solvent: CD$_3$CN): 2.89 s (CH$_3$).

EXAMPLE 2

Hexamethylguanidinium tris(pentafluoroethyl)trifluorophosphate

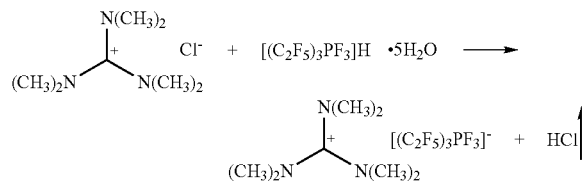

5.00 g (27.8 mmol) of hexamethylguanidinium chloride are dissolved in 150 cm³ of water. 15.38 g (28.7 mmol) of tris(pentafluoroethyl)trifluorophosphoric acid pentahydrate are added at room temperature while the reaction mixture is stirred using a magnetic stirrer. The precipitate is filtered off, washed four times with 50 cm³ of water and dried at 50-60° C. under a vacuum of 7.0 Pa, giving 16.2 g of a solid material (m.p.=128-129° C.). The yield of hexamethylguanidinium tris(pentafluoroethyl)trifluorophosphate is 98.9%, based on hexamethylguanidinium chloride.

$^{19}$F NMR (reference: CCl$_3$F—internal standard; solvent: CD$_3$CN): −43.50 dm (PF); −79.52 m (CF$_3$); −81.21 m (2CF$_3$); −86.87 dm (PF$_2$); −114.91 m (CF$_2$); −115.49 m (2CF$_2$); $^1J_{P,F}$=889 Hz; $^1J_{P,F}$=901 Hz; $^2J_{P,F}$=85 Hz; $^2J_{P,F}$=98 Hz.

$^1$H NMR (reference: TMS; solvent: CD$_3$CN): 2.89 s (CH$_3$).

$^{31}$P NMR (reference: 85% H$_3$PO$_4$; solvent: CD$_3$CN): −148.59 dtm;

$^1J_{P,F}$=890 Hz; $^1J_{P,F}$=902 Hz.

Elemental Analysis

Found, %: C, 26.57; H, 3.05; N, 7.15.

Calculated for C$_{13}$H$_{18}$F$_{18}$N$_3$P, %: C, 26.50; H, 3.08; N, 7.13.

EXAMPLE 3

N,N,N',N',N''-pentamethyl-N''-n-propylguanidinium triflate

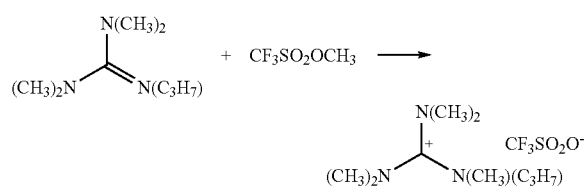

10.47 g (66.6 mmol) of N,N,N',N'-tetramethyl-N''-n-propylguanidine are dissolved in 80 cm³ of pentane. 10.94 g (66.7 mmol) of methyl triflate, CF$_3$SO$_2$OCH$_3$, are slowly added (dropwise) at room temperature while the reaction mixture is stirred vigorously using a magnetic stirrer. The precipitate is filtered off and washed with 40 cm³ of pentane and dried at 50-60° C. under a vacuum of 7.0 Pa, giving 21.4 g of a solid material (m.p.=109-110° C.). The yield of N,N,N',N',N''-pentamethyl-N''-n-propylguanidinium triflate is approximately quantitative.

$^{19}$F NMR (reference: CCl$_3$F—internal standard; solvent: CD$_3$CN): −77.89 s (CF$_3$).

$^1$H NMR (reference: TMS; solvent: CD$_3$CN): 0.91 t (CH$_3$); 1.56 br.s (1H, CH$_2$); 1.70 br.s (1H,CH$_2$); 3.13 m (CH$_2$); 2.88 s (CH$_3$); 2.90 s (4CH$_3$); $^3J_{H,H}$=7.3 Hz.

EXAMPLE 4

N,N,N',N',N''-pentamethyl-N''-i-propylguanidinium triflate

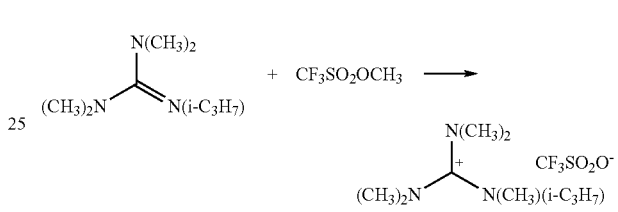

8.27 g (52.6 mmol) of N,N,N',N'-tetramethyl-N''-i-propylguanidine are dissolved in 80 cm³ of pentane. 8.64 g (52.7 mmol) of methyl triflate, CF$_3$SO$_2$OCH$_3$, are slowly added (dropwise) at room temperature while the reaction mixture is stirred vigorously using a magnetic stirrer. The precipitate is filtered off and washed with 40 cm³ of pentane and dried at 50-60° C. under a vacuum of 7.0 Pa, giving 16.9 g of a solid material (m.p.=103-105° C.). The yield of N,N,N',N',N''-pentamethyl-N''-i-propylguanidinium triflate is approximately quantitative.

$^{19}$F NMR (reference: CCl$_3$F—internal standard; solvent: CD$_3$CN): −77.91 s (CF$_3$).

$^1$H NMR (reference: TMS; solvent: CD$_3$CN): 1.20 br.s (CH$_3$); 1.32 br.s (CH$_3$); 2.77 s (CH$_3$); 2.91 s (4CH$_3$); 3.74 hep. (CH); $^3J_{H,H}$=6.6 Hz.

EXAMPLE 5

N,N,N',N',N''-pentamethyl-N''-n-propylguanidinium tris(pentafluoroethyl)trifluorophosphate

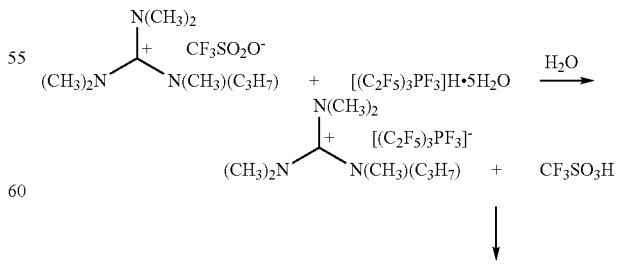

8.00 g (24.9 mmol) of N,N,N',N',N''-pentamethyl-N''-n-propylguanidinium triflate are dissolved in 100 cm³ of water, and 13.40 g (25.0 mmol) of tris-(pentafluoroethyl)trifluorophosphoric acid pentahydrate are added at room temperature while the reaction mixture is stirred vigorously using a magnetic stirrer. The reaction mixture is cooled using an ice bath, and the aqueous solution (upper phase) is decanted off. The viscous liquid (lower phase) is washed three times with 30 cm³ of ice-water. The residue is dried at 50-60° C. under a vacuum of 7.0 Pa, giving 14.2 g of a liquid. The yield of N,N,N', N', N"-pentamethyl-N"-n-propylguanidinium tris(pentafluoroethyl)trifluorophosphate is 92.4%, based on N,N,N',N',N"-pentamethyl-N"-n-propylguanidinium triflate.

$^{19}$F NMR (reference: CCl$_3$F—internal standard; solvent: CD$_3$CN): −43.54 dm (PF); −79.54 m (CF$_3$); −81.22 m (2CF$_3$); −86.91 dm (PF$_2$); −114.88 m (CF$_2$); −115.49 m (2CF$_2$); $^1J_{P,F}$=890 Hz; $^1J_{P,F}$=901 Hz; $^2J_{P,F}$=84 Hz; $^2J_{P,F}$=98 Hz.

$^1$H NMR (reference: TMS; solvent: CD$_3$CN): 0.92 t (CH$_3$); 1.56 br.s (1H,CH$_2$); 1.72 br.s (1H,CH$_2$); 3.13 m (CH$_2$); 2.88 s (CH$_3$); 2.90 s (4CH$_3$); $^3J_{H,H}$=7.3 Hz.

$^{31}$P NMR (reference: 85% H$_3$PO$_4$; solvent: CD$_3$CN): −148.53 dtm;
$^1J_{P,F}$=890 Hz; $^1J_{P,F}$=902 Hz.

EXAMPLE 6

N,N,N',N',N"-pentamethyl-N"-i-propylguanidinium tris(pentafluoroethyl)trifluorophosphate

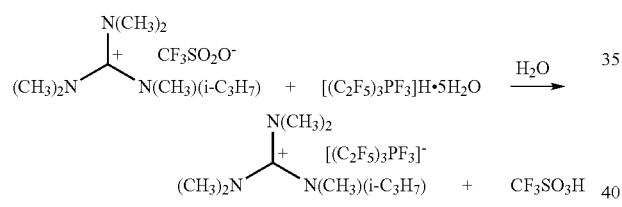

6.80 g (21.2 mmol) of N,N,N',N',N"-pentamethyl-N"-i-propylguanidinium triflate are dissolved in 100 cm³ of water. 11.40 g (21.3 mmol) of tris(pentafluoroethyl)trifluorophosphoric acid pentahydrate are added at room temperature while the reaction mixture is stirred vigorously using a magnetic stirrer. The residue is filtered off, washed three times with 30 cm³ of ice-water and dried at 50-60° C. under a vacuum of 7.0 Pa, giving 12.3 g of a solid material (m.p.=68-69° C.). The yield of N,N,N',N',N"-pentamethyl-N"-i-propylguanidinium tris(pentafluoroethyl)trifluorophosphate is 94.0%, based on N,N,N',N',N"-pentamethyl-N"-i-propylguanidinium triflate.

$^{19}$F NMR (reference: CCl$_3$F—internal standard; solvent: CD$_3$CN): −43.52 dm (PF); −79.55 m (CF$_3$); −81.21 m (2CF$_3$); −86.84 dm (PF$_2$); −114.89 m (CF$_2$); −115.50 m (2CF$_2$); $^1J_{P,F}$=889 Hz; $^1J_{P,F}$=901 Hz; $^2J_{P,F}$=87 Hz; $^2J_{P,F}$=97 Hz.

$^1$H NMR (reference: TMS; solvent: CD$_3$CN): 1.22 br.s (CH$_3$); 1.33 br.s (CH$_3$); 2.77 s (CH$_3$); 2.91 s (4CH$_3$); 3.74 hep. (CH); $^3J_{H,H}$=6.6 Hz.

$^{31}$P NMR (reference: 85% H$_3$PO$_4$; solvent: CD$_3$CN): −148.56 dtm;
$^1J_{P,F}$=890 Hz; $^1J_{P,F}$=902 Hz.

EXAMPLE 7

Guanidinium triflate

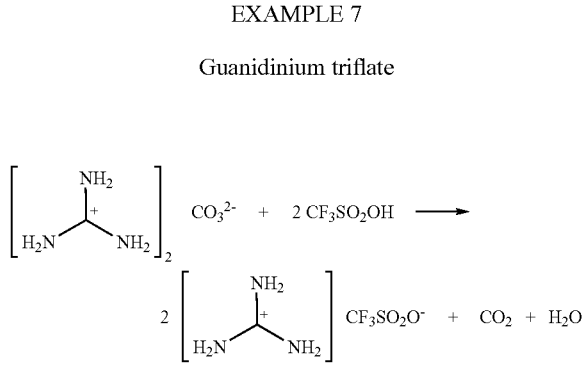

6.5 g (36.1 mmol) of guanidinium carbonate are dissolved in 100 cm³ of water. 10.9 g (72.6 mmol) of trifluoromethanesulfonic acid are added at room temperature while the reaction mixture is stirred vigorously using a magnetic stirrer. The flask containing the reaction mixture is cooled using ice, and the precipitate is filtered off and washed twice with 30 cm³ of ice-water. The residue is dried at 50-60° C. under a vacuum of 7.0 Pa, giving 14.1 g of a solid material (m.p.=152-153° C.). The yield of guanidinium triflate is 93.4%, based on guanidinium carbonate.

$^{19}$F NMR (reference: CCl$_3$F—internal standard; solvent: CD$_3$CN): −78.24 s (CF$_3$).

$^1$H NMR (reference: TMS; solvent: CD$_3$CN): 6.20 br.s (NH).

EXAMPLE 8

Guanidinium tris(pentafluoroethyl)trifluorophosphate

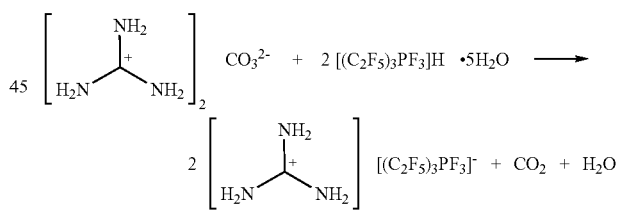

10.67 g (59.2 mmol) of guanidinium carbonate are dissolved in 250 cm³ of water. 63.5 g (118.4 mmol) of tris(pentafluoroethyl)trifluorophosphoric acid pentahydrate are added at room temperature while the reaction mixture is stirred vigorously using a magnetic stirrer. The flask containing the reaction mixture is cooled using ice, and the lower phase is separated off and washed twice with 30 cm³ of ice-water. The residue is dried at 50-60° C. under a vacuum of 7.0 Pa, giving 53.2 g of a solid material (m.p.=121-123° C.). The yield of guanidinium tris(pentafluoroethyl)trifluorophosphate is 89.0%.

$^{19}$F NMR (reference: CCl$_3$F—internal standard; solvent: CD$_3$CN): −43.48 dm (PF); −79.54 m (CF$_3$); −81.23 m (2CF$_3$); −86.87 dm (PF$_2$); −114.89 m (CF$_2$); −115.47 m (2CF$_2$); $^1J_{P,F}$=888 Hz; $^1J_{P,F}$=901 Hz; $^2J_{P,F}$=84 Hz; $^2J_{P,F}$=98 Hz.

$^1$H NMR (reference: TMS; solvent: CD$_3$CN): 5.94 br.s (NH).
$^{31}$P NMR (reference: 85% H$_3$PO$_4$; solvent: CD$_3$CN): −148.53 dtm;
$^1J_{P,F}$=888 Hz; $^1J_{P,F}$=902 Hz.

EXAMPLE 9

N,N,N',N'-tetramethyl-N''-ethylguanidinium triflate

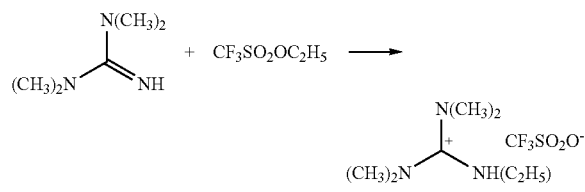

30.0 g (260.5 mmol) of N,N,N',N'-tetramethylguanidine are dissolved in 150 cm$^3$ of pentane, and 47.3 g (265.5 mmol) of ethyl triflate, CF$_3$SO$_2$OC$_2$H$_5$, are slowly added (dropwise) over the course of 30 min with ice-bath cooling and while the reaction mixture is stirred vigorously using a magnetic stirrer. The reaction mixture is stirred at room temperature for a further 10 min. The liquid lower phase is separated off and washed twice with 50 cm$^3$ of pentane. The residue is dried at 40-50° C. for one hour under a vacuum of 7.0 Pa, giving 75.0 g of a liquid material. The yield of N,N,N',N'-tetramethyl-N''-ethylguanidinium triflate is 98.2%. The material is characterised by $^{19}$F and $^1$H NMR spectroscopy, which show the formation of two isomers of N,N,N',N'-tetramethyl-N''-ethylguanidinium triflate.

$^{19}$F NMR (reference: CCl$_3$F—internal standard; solvent: CD$_3$CN): −77.95 s (CF$_3$).

$^1$H NMR (reference: TMS; solvent: CD$_3$CN): 1.15 t (CH$_3$); 1.22 t (CH$_3$); 2.89 br.s (CH$_3$); 2.91 br.s (CH$_3$); 2.92 s (2CH$_3$); 2.93 br.s (4CH$_3$); 3.22 q (CH$_2$); 5.47 s (NH); 6.04 br.s (NH); $^3J_{H,H}$=7.2 Hz.

Elemental Analysis
Found, %: C, 32.82; H, 6.26; N, 14.25.
Calculated for C$_8$H$_{18}$F$_3$N$_3$O$_3$S, %: C, 32.76; H, 6.19; N, 14.33.

EXAMPLE 10

N,N,N',N'-tetramethyl-N''-ethylguanidinium tris(pentafluoroethyl)trifluorophosphate

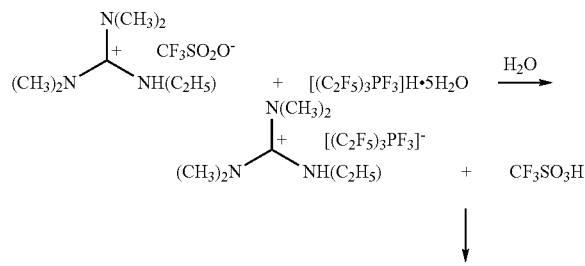

29.7 g (101.3 mmol) of N,N,N',N'-tetramethyl-N''-ethylguanidinium triflate are dissolved in 100 cm$^3$ of water, and 57.0 g (106.3 mmol) of tris(pentafluoroethyl)trifluorophosphoric acid pentahydrate are added at room temperature while the reaction mixture is stirred vigorously using a magnetic stirrer. The lower liquid phase is separated off and washed four times with 50 cm$^3$ of water. The residue is dried at 70° C. in an oil bath for three hours under a vacuum of 7.0 Pa, giving 56.1 g of a liquid material. The yield of N,N,N',N'-tetramethyl-N''-ethylguanidinium tris(pentafluoroethyl)trifluorophosphate is 94.0%, based on N,N,N',N'-tetramethyl-N''-ethylguanidinium triflate.

The material is characterised by $^{19}$F, $^1$H and $^{31}$P NMR spectroscopy, which shows the formation of two isomers of N,N,N',N'-tetramethyl-N''-ethylguanidinium tris(pentafluoroethyl)trifluorophosphate.

$^{19}$F NMR (reference: CCl$_3$F—internal standard; solvent: CD$_3$CN): −43.55 dm (PF); −79.58 m (CF$_3$); −81.27 m (2CF$_3$); −86.93 dm (PF$_2$); −114.93 m (CF$_2$); −115.51 m (2CF$_2$); $^1J_{P,F}$=889 Hz; $^1J_{P,F}$=901 Hz; $^2J_{P,F}$=85 Hz; $^2J_{P,F}$=97 Hz.

$^1$H NMR (reference: TMS; solvent: CD$_3$CN): 1.16 t (CH$_3$); 1.23 t (CH$_3$); 2.89 br.s (CH$_3$); 2.91 br.s (CH$_3$); 2.93 br.s (4CH$_3$); 2.94 s (2CH$_3$); 3.22 q (CH$_2$); 3.24 q (CH$_2$); 5.80 br. s (NH); 6.14 br.s (NH); $^3J_{H,H}$=7.2 Hz.

$^{31}$P NMR (reference: 85% H$_3$PO$_4$; solvent: CD$_3$CN): −148.58 dtm;
$^1J_{P,F}$=888 Hz; $^1J_{P,F}$=902 Hz.

EXAMPLE 11

1,3-Dimethyl-2-diethylaminoimidazolidinium chloride

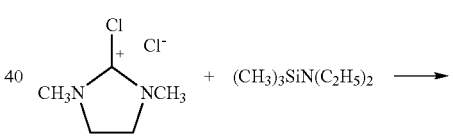

30.0 g (177.5 mmol) of 1,3-dimethyl-2-chloroimidazolidinium chloride are dissolved in 70 cm$^3$ of dry chloroform, and 27.1 g (186.5 mmol) of trimethylsilyldiethylamine (CH$_3$)$_3$SiN(C$_2$H$_5$)$_2$ are added slowly (dropwise) over the course of 30 min with ice-bath cooling and while the reaction mixture is stirred vigorously using a magnetic stirrer. The reaction mixture is subsequently stirred overnight at room temperature. The solvent is removed under reduced pressure. The residue is washed twice with 30 cm$^3$ of hexane and dried at 60° C. for one hour under a vacuum of 7.0 Pa, giving 35.7 g of a crystalline material. The yield of 1,3-dimethyl-2-diethylaminoimidazolidinium chloride is 97.8%, based on 1,3-dimethyl-2-chloroimidazolidinium chloride.

$^1$H NMR (reference: TMS; solvent: CD$_3$CN): 1.16 t (2CH$_3$); 2.94 s (2CH$_3$); 3.33 q (2CH$_2$); 3.71 s (2 CH$_2$); $^3J_{H,H}$=7.1 Hz.

EXAMPLE 12

1,3-Dimethyl-2-diethylaminoimidazolidinium tris(pentafluoroethyl)trifluorophosphate

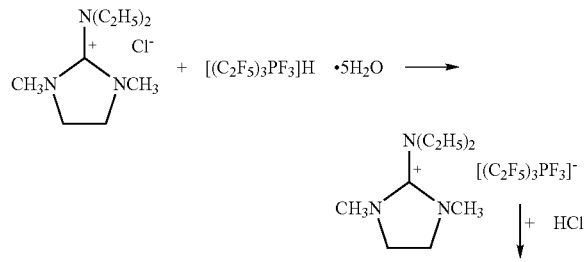

15.0 g (72.9 mmol) of 1,3-dimethyl-2-diethylaminoimidazolidinium chloride are dissolved in 200 cm$^3$ of water, and 41.0 g (76.5 mmol) of tris(pentafluoroethyl)trifluorophosphoric acid pentahydrate are added at room temperature while the reaction mixture is stirred vigorously using a magnetic stirrer. The precipitate is filtered off and washed three times with 50 cm$^3$ of water. The residue is dried at 50-60° C. in an oil bath for three hours under a vacuum of 7.0 Pa, giving 43.9 g of a solid white material (m.p. 36-37° C.). The yield of 1,3-dimethyl-2-diethylaminoimidazolidinium tris(pentafluoroethyl)trifluorophosphate is 97.8%, based on 1,3-dimethyl-2-diethylaminoimidazolidinium chloride.

$^{19}$F NMR (reference: CCl$_3$F—internal standard; solvent: CD$_3$CN): −43.54 dm (PF); −79.57 m (CF$_3$); −81.26 m (2CF$_3$); −86.90 dm (PF$_2$); −114.92 m (CF$_2$); −115.51 m (2CF$_2$); $^1J_{P,F}$=888 Hz; $^1J_{P,F}$=900 Hz; $^2J_{P,F}$=85 Hz; $^2J_{P,F}$=98 Hz.

$^1$H NMR (reference: TMS; solvent: CD$_3$CN): 1.20 t (2CH$_3$); 2.94 s (2CH$_3$); 3.34 q (2CH$_2$); 3.68 s (2CH$_2$); $^3J_{H,H}$=7.1 Hz.

$^{31}$P NMR (reference: 85% H$_3$PO$_4$; solvent: CD$_3$CN): −148.57 dtm;

$^1J_{P,F}$=890 Hz; $^1J_{P,F}$=902 Hz.

Elemental Analysis

Found, %: C, 29.18; H, 2.94; N, 7.02.

Calculated for C$_{15}$H$_{20}$F$_{18}$N$_3$P, %: C, 29.28; H, 3.28; N, 6.83.

EXAMPLE 13

1,3-Dimethyl-2-diethylaminoimidazolidinium triflate

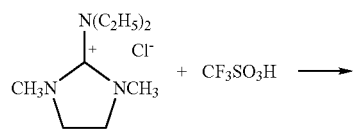

-continued

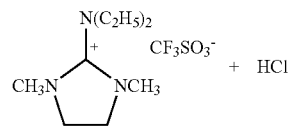

10.98 g (53.4 mmol) of 1,3-dimethyl-2-diethylaminoimidazolidinium chloride are dissolved in 70 cm$^3$ of water, and 8.24 g (54.9 mmol) of trifluoromethanesulfonic acid are added at room temperature over the course of 5 min while the reaction mixture is stirred vigorously using a magnetic stirrer. The reaction mixture is stirred at room temperature for a further 5 min. All volatile components of the mixture are removed under reduced pressure. The residue is washed twice with 50 cm$^3$ of diethyl ether and dried at 60° C. in an oil bath for three hours under a vacuum of 7.0 Pa, giving 16.7 g of a crystalline material (m.p. 67-68° C.). The yield of 1,3-dimethyl-2-diethyl-aminoimidazolidinium triflate is 97.9%, based on 1,3-dimethyl-2-diethyl-aminoimidazolidinium chloride.

$^{19}$F NMR (reference: CCl$_3$F—internal standard; solvent: CD$_3$CN): −77.92 s (CF$_3$).

$^1$H NMR (reference: TMS; solvent: CD$_3$CN): 1.18 t (2CH$_3$); 2.94 s (2CH$_3$); 3.34 q (2CH$_2$); 3.69 s (2CH$_2$); $^3J_{H,H}$=7.1 Hz.

EXAMPLE 14

Hexamethylguanidinium tetracyanoborate

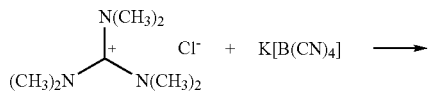

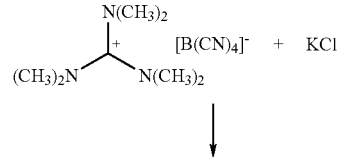

4.54 g (29.5 mmol) of potassium tetracyanoborate are dissolved in 100 cm$^3$ of water, and a solution of 5.30 g (29.5 mmol) of hexamethylguanidinium chloride in 15 cm$^3$ of water is added at room temperature while the reaction mixture is stirred vigorously using a magnetic stirrer. The reaction mixture is stirred at room temperature for a further 20 min. The precipitate is filtered off and washed twice with 10 cm$^3$ of water. The residue is dried at 60° C. in an oil bath for three hours under a vacuum of 7.0 Pa, giving 5.50 g of a solid white material (m.p. 123-124° C.). The yield of hexamethylguanidinium tetracyanoborate is 72.0%, based on hexamethylguanidinium chloride.

$^1$H NMR (reference: TMS; solvent: CD$_3$CN): 2.90 s (CH$_3$).
$^{11}$B NMR (reference: BF$_3$ ? O(C$_2$H$_5$)$_2$; solvent: CD$_3$CN): −38.23 s.

EXAMPLE 15

Hexamethylguanidinium pentafluoroethyltrifluoroborate

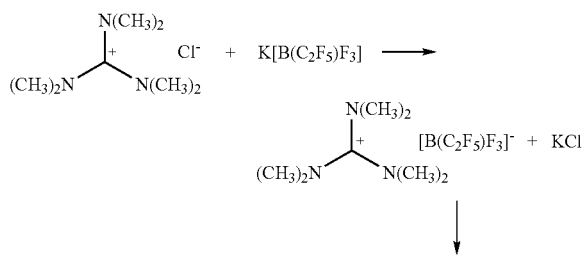

0.40 g (2.23 mmol) of hexamethylguanidinium chloride is dissolved in 2 cm$^3$ of water, and a solution of 0.51 g (2.26 mmol) of potassium pentafluoroethyltrifluoroborate in 3 cm$^3$ of water is added at room temperature while the reaction mixture is stirred vigorously using a magnetic stirrer. The reaction mixture is stirred at room temperature for a further 20 min. The precipitate is filtered off and washed twice with 3 cm$^3$ of water. The residue is dried for three hours at 55-60° C. in an oil bath under a vacuum of 7.0 Pa, giving 0.69 g of a solid white material (m.p. 78-79° C.). The yield of hexamethylguanidinium pentafluoroethyltrifluoroborate is 93.5%, based on hexamethylguanidinium chloride.

$^{19}$F NMR (reference: CCl$_3$F—internal standard; solvent: CD$_3$CN): −83.08 q (CF$_3$); −135.79 q (CF$_2$) −152.82 q,q (BF$_3$); $^4J_{F,F}$=4.8 Hz; $^2J_{B,F}$=19.3 Hz;
$^1J_{B,F}$=40.7 Hz.
$^1$H NMR (reference: TMS; solvent: CD$_3$CN): 2.89 s (6CH$_3$).
$^{11}$B NMR (reference: BF$_3$ ? O(C$_2$H$_5$)$_2$; solvent: CD$_3$CN): −0.28 q,t.

EXAMPLE 16

1,3-Dimethyl-2-diethylaminoimidazolidinium tetrafluoroborate

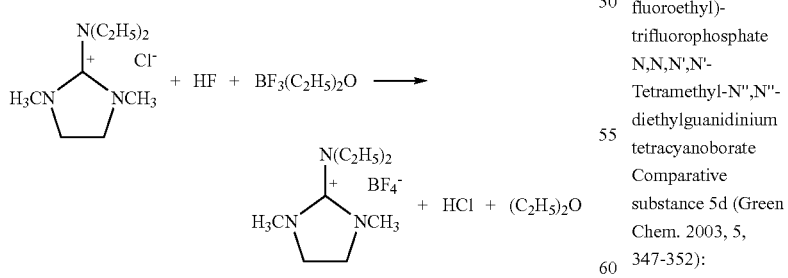

8.77 g (42.6 mmol) of 1,3-dimethyl-2-diethylaminoimidazolidinium chloride are initially introduced in a PFA flask. 4.76 g (236.8 mmol) of anhydrous hydrofluoric acid are added over the course of 3 min with vigorous stirring and cooling using an ice bath. The reaction mixture is stirred with ice-bath cooling for a further 20 min, and then 6.35 g (44.7 mmol) of boron trifluoride etherate are added over the course of 5 min while the reaction mixture is stirred vigorously using a magnetic stirrer. The reaction mixture is stirred at room temperature for a further hour, and then all volatile components of the mixture are removed under reduced pressure. The residue is dried at 90-105° C. in an oil bath for two hours under a vacuum of 1.3 Pa, giving 9.17 g of a crystalline material (m.p. 58-60° C.). The yield of 1,3-dimethyl-2-diethylaminoimidazolidinium tetrafluoroborate is 88.7%, based on 1,3-dimethyl-2-diethylaminoimidazolidinium chloride.

$^{19}$F NMR (reference: CCl$_3$F—internal standard; solvent: CD$_3$CN): −150.42 s; −150.47 s (BF$_4^-$).
$^1$H NMR (reference: TMS; solvent: CD$_3$CN): 1.19 t (2CH$_3$); 2.94 s (2CH$_3$); 3.34 q (2CH$_2$); 3.68 (2CH$_2$); $^3J_{H,H}$= 7.1 Hz.

EXAMPLE 17

The viscosities of the guanidinium compounds, listed in Table 1, are measured on an SVM3000 viscometer from Anton Paar, Austria, using the standard procedure described in the manual accompanying the viscometer.

TABLE 1

| | Viscosity data | | | |
|---|---|---|---|---|
| Compound | Viscosity, cP (mPa · s) at 20° C. | 40° C. | 60° C. | 80° C. |
| 1,3-Dimethyl-2-dibutylaminoimidazolidinium tris(pentafluoroethyl)-trifluorophosphate | 376 | 107 | 43 | 21 |
| 1,3-Dimethyl-2-diethylaminoimidazolidinium tris(pentafluoroethyl)-trifluorophosphate | | 78 | 34 | 18 |
| N,N,N',N'-Tetramethyl-N''-ethyl-guanidinium tris(pentafluoroethyl)-trifluorophosphate | 164 | 57 | 27 | 15 |
| N,N,N',N'-Tetramethyl-N'',N''-diethylguanidinium tetracyanoborate | 47 | 22 | 13 | 8 |
| Comparative substance 5d (Green Chem. 2003, 5, 347-352): N,N-dimethyl-N',N',N'',N''-tetrahexylguanidinium bis(trifluoromethanesulfonyl)imide | 346 (25° C.) | 269 | 124 | |

The invention claimed is:

1. A process for the preparation of a guanidinium salt of the formula I

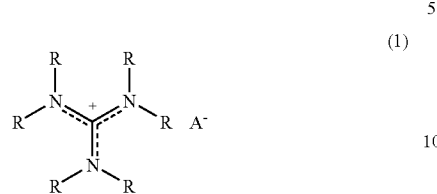

in which
R=H, straight-chain or branched alkyl having 1-20 C atoms, or in the case $A^-=[(C_2F_5)_3PF_3]^-$ than R is a straight chain or branched alkyl having 2-20 C atoms, partially or fully unsaturated cycloalkyl having 3-7 C atoms, which may be substituted by alkyl groups having 1-6 C atoms, where the R are in each case identical or different, where up to four R may be connected to one another in pairs by a single or double bond, where one or more R may be partially or fully substituted by halogens, or partially by —CN or —$NO_2$, and where one or two non-adjacent carbon atoms of the R may be replaced by —O—, —C(O)—, —C(O)O—, —S—, —S(O)—, —$SO_2$—, —$SO_2O$—, —N=, —N=N—, —NH—, —NR'—, —PR'—, —P(O)R'—, —P(O)R'—O—, —O—P(O)R'—O—, —P(O)(NR'$_2$)—NR'— or —PR'$_2$=N—, R'=unfluorinated, partially or perfluorinated $C_1$- to $C_6$-alkyl, $C_3$- to $C_7$-cycloalkyl, unsubstituted or substituted phenyl or an unsubstituted or substituted heterocycle, $A^-=[BF_4]^-$, $[(FSO_2)_2N]^-$, $[R^FCF_2SO_3]^-$, $[(R^{F'}SO_2)_2N]^-$, $[(R^{F'}SO_2)_3C]^-$, $[(FSO_2)_3C]^-$, $[R^FCF_2C(O)O]^-$, $[P(C_nF_{2n+1-m}H_m)_yF_{6-y}]^-$, $[P(C_6F_5)_yF_{6-y}]^-$, $[R^F{}_2P(O)O]^-$, $[R^FP(O)O_2]^{2-}$, $[BF_2R^F{}_{4-2}]^-$, $[BF_2(CN)_{4-2}]^-$, $[N(CF_3)_2]^-$, $[N(CN)_2]^-$, $[C(CN)_3]^-$ or

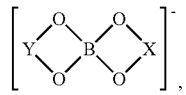

$R^F$=perfluorinated and straight-chain or branched alkyl having 1-20 C atoms, perfluorinated and straight-chain or branched alkenyl having 2-20 C atoms and one or more double bonds, perfluorinated and straight-chain or branched alkynyl having 2-20 C atoms and one or more triple bonds, perfluorinated and saturated, partially or fully unsaturated cycloalkyl having 3-7 C atoms, which may be substituted by perfluoroalkyl groups, where a plurality of $R^F$ may in each case be identical or different, where the $R^F$ may be connected to one another in pairs by a single or double bond, and where one or two non-adjacent carbon atoms of the $R^F$ which are not in the α-position to the heteroatom may be replaced by —O—, —$SO_2$— or —NR'— or by the end group —$SO_2X'$, R'=unfluorinated, partially or perfluorinated $C_1$- to $C_6$-alkyl, $C_3$- to $C_7$-cycloalkyl, unsubstituted or substituted phenyl, including —$C_6F_5$, or an unsubstituted or substituted heterocycle, X'=F, Cl or Br, $R^{F'}$=perfluorinated and straight-chain or branched alkyl having 2-20 C atoms, perfluorinated and straight-chain or branched alkenyl having 2-20 C atoms and one or more double bonds, perfluorinated and straight-chain or branched alkynyl having 2-20 C atoms and one or more triple bonds, perfluorinated and saturated, partially or fully unsaturated cycloalkyl having 3-7 C atoms, in particular phenyl, which may be substituted by perfluoroalkyl groups, where a plurality of $R^{F'}$ may in each case be identical or different, where the $R^{F'}$ may be connected to one another in pairs by a single or double bond, and where one or two non-adjacent carbon atoms of the $R^{F'}$ which are not in the α-position to the heteroatom may be replaced by —O—, —$SO_2$— or —NR'— or by the end group —$SO_2X'$, R'=unfluorinated, partially or perfluorinated $C_1$- to $C_6$-alkyl, $C_3$- to $C_7$-cycloalkyl, unsubstituted or substituted phenyl, including —$C_6F_5$, or an unsubstituted or substituted heterocycle, and X'=F, Cl or Br, n=1 to 20, preferably 1 to 12, and m=0, 1, 2 or 3 and y=1, 2, 3 or 4 and z=0, 1, 2 or 3 and —X— and —Y— are in each case identical or different and denote —C(O)—C(O)—, —C(O)—$(CH_2)_4$—C(O)—, q=1, 2 or 3, —C(O)—$(CF_2)_q$—C(O)—, where q=1, 2 or 3, —C($CF_3$)$_2$—C($CF_3$)$_2$—,

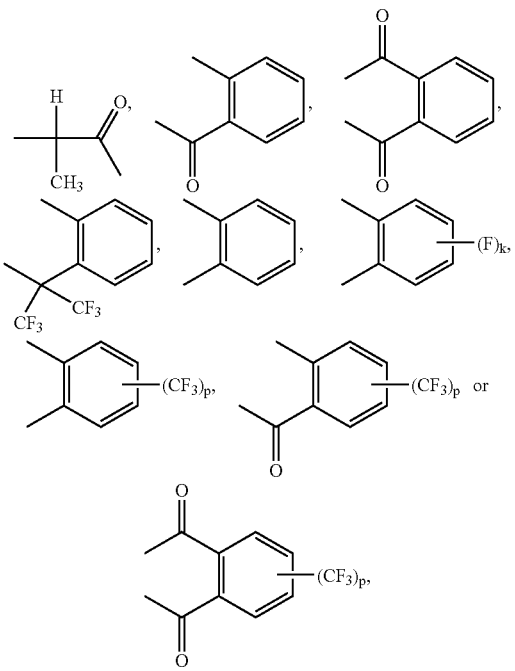

where k=1, 2, 3 or 4 and p=1 or 2 wherein a guanidine $(NR_2)_2C=(NR)$ or a guanidinium salt $C(NR_2)_3{}^+X^-$, where $X^-$ is selected from the group $F^-$, $Cl^-$, $Br^-$, $I^-$, $[HF_2]^-$, $[CN]^-$, $[SCN]^-$, $[CH_3COO]^-$, $[CF_3COO]^-$, $[CF_3SO_3]^-$, $[CH_3OSO_3]^-$, $[SiF_6]^{2-}$, $[BF_4]$,

[SO$_4$]$^{2-}$, [NO$_3$]$^-$, tosylates, malonates, substituted malonates and [CO$_3$]$^-$, is reacted with an acid AH or a salt Kt$^-$A$^-$, and Kt is an alkali or alkaline earth metal and wherein the reaction is carried our at a temperature at which at least one of the components is liquid.

2. A process for the preparation of a salt according to claim 1, wherein guanidinium chloride C(NR$_2$)$_3$$^+$Cl$^-$ or guanidinium bromide C(NR$_2$)$_3$$^+$Br, is reacted with anhydrous HF, and the guanidinium fluoride formed in situ is subsequently reacted with boron trifluoride etherate BF$_3$*Et$_2$O.

3. A process according to claim 1, wherein the reaction is carried out with an up to 10% excess or preferably with an equimolar amount of boron trifluoride etherate in relation to the guanidinium salt.

4. A process according to claim 1, wherein R is hydrogen and/or a straight-chain or branched alkyl having 1-12 C atoms.

5. A process according to claim 1, wherein R is selected from the group methyl, ethyl, n-propyl, isopropyl, n-butyl, tert-butyl, sec-butyl, phenyl and cyclohexyl.

6. A process according to claim 1, wherein at least two substituents R are connected to one another by single or double bonds in such a way that a monocyclic cation is formed.

7. A process according to claim 1, wherein R$^F$ =perfluorinated and straight-chain or branched alkyl having 1-12 C atoms.

8. A process according to claim 1, wherein A$^-$ is [(FSO$_2$)$_2$N]—, [CF$_3$CF$_2$SO$_3$]$^-$, [(C$_2$F$_5$SO$_2$)$_2$N], [(C$_2$F$_5$SO$_2$)$_3$C]$^-$, [(FSO$_2$)$_3$C]$^-$, [CF$_3$CF$_2$C(O)O]$^-$, [P(C$_2$F$_5$)$_3$F$_3$]$^-$, [P(CF$_3$)$_3$F$_3$]$^-$, [P(C$_2$F$_4$H)(CF$_3$)$_2$F$_3$]$^-$, [P(C$_2$F$_3$H$_2$)$_3$F$_3$]$^-$, [P(C$_2$F$_5$)(CF$_3$)$_2$F$_3$]$^-$, [P(C$_6$F$_5$)$_3$F$_3$]$^-$, [P(C$_3$F$_7$)$_3$F$_3$]$^-$, [P(C$_4$F$_9$)$_3$F$_3$]$^-$, [P(C$_2$F$_5$)$_2$F$_4$]$^-$, [(C$_2$F$_5$)$_2$P(O)O]$^-$, [(C$_3$F$_5$)P(O)O$_2$]$^{2-}$, [P(C$_6$F$_5$)$_2$F$_4$]$^-$, [(CF$_3$)$_2$P(O)O]$^-$, [(C$_4$F$_9$)$_2$P(O)O], [CF$_3$P(O)O$_2$]$^{2-}$, [BF$_3$(CF$_3$)]$^-$, [BF$_2$(C$_2$F$_5$)$_2$]$^-$, [BF$_3$(C$_2$F$_5$)]$^-$, [BF$_2$(CF$_3$)$_2$]$^-$, [B(C$_2$F$_5$)$_4$]$^-$, [BF$_3$(CN)]$^-$, [BF$_2$(CN)$_2$]$^-$, [B(CN)$_4$]$^-$, [B(CF$_3$)$_4$]$^-$, [N(CF$_3$)$_2$]$^-$, [N(CN$_2$)$_2$]$^-$, [C(CN)$_3$]$^-$,

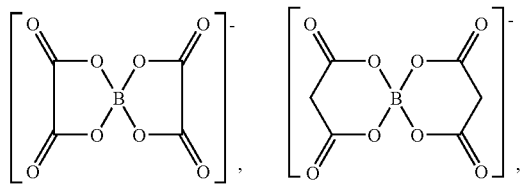

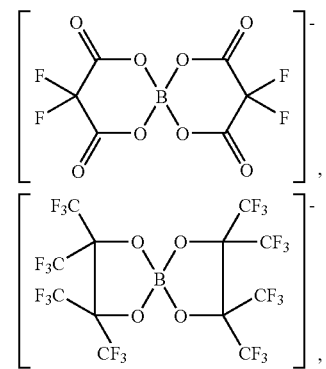

-continued

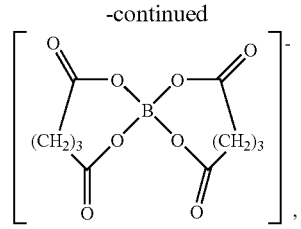

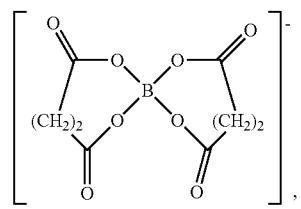

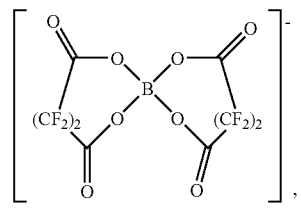

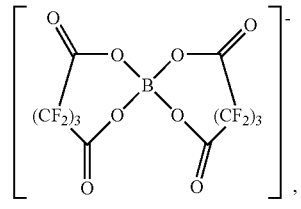

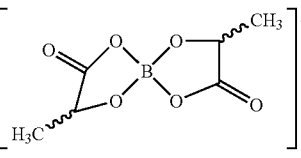

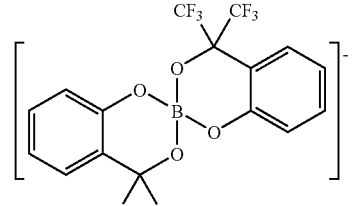

or

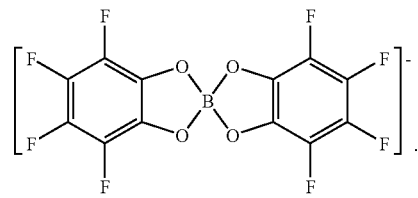

* * * * *